US007078547B2

(12) United States Patent
Deng et al.

(10) Patent No.: US 7,078,547 B2
(45) Date of Patent: Jul. 18, 2006

(54) CATALYTIC ASYMMETRIC CYANOSILYLATION OF KETONES, ALDEHYDES, THIOKETONES, THIOALDEHYDES, IMINES AND HYDRAZONES

(75) Inventors: Li Deng, Waltham, MA (US); Shi-Kai Tian, Waltham, MA (US)

(73) Assignee: Brandeis University, Waltham, MA (US)

( * ) Notice: Subject to any disclaimer, the term of this patent is extended or adjusted under 35 U.S.C. 154(b) by 339 days.

(21) Appl. No.: 10/358,990

(22) Filed: Feb. 5, 2003

(65) Prior Publication Data

US 2003/0236226 A1    Dec. 25, 2003

Related U.S. Application Data

(60) Provisional application No. 60/356,993, filed on Feb. 13, 2002.

(51) Int. Cl.
C07F 7/04 (2006.01)

(52) U.S. Cl. .................................................. 556/415

(58) Field of Classification Search ................. 556/415
See application file for complete search history.

(56) References Cited

OTHER PUBLICATIONS

Evans, D.A., "A New Selective Carbonyl Blocking Group", Journal of the American Chemical Society, vol. 95 No. 17, pp. 5822-5823, (Aug. 1973).

Chemical Abstract Online, abstract No. 1999:98346, Jenner, Gerard, "Addition of trimethylsilyl cyanide to aromatic ketones promoted by organic solutions of lithium salts", (1999).

International Search Report completed Jun. 2, 2003 and mailed Aug. 22, 2003.

Belokon et al; "Optimized Catalysts for the Asymmetric Addition of Trimethylsiyl Cyanide to Aldehydes and Ketones", Tetrahedron 57:771-779, (2001).

Belokon et al.; "The Asymmetric Addition of Trimethylsilyl Cyanide to Ketones Catalyzed by a Bimetallic, Chiral (Salen) Titanium Complex", Tetrahedron Letters 40: 8147-8150, (1999).

(Continued)

*Primary Examiner*—Samuel Barts
(74) *Attorney, Agent, or Firm*—Dana M. Gordon; Foley Hoag LLP

(57) ABSTRACT

One aspect of the present invention relates to a method for the catalytic asymmetric cyanosilylation of ketones, aldehydes, thioketones, thioaldehydes, imines and hydrazones. The critical elements of the method are: a non-racemic chiral tertiary-amine-containing catalyst; a substrate selected from the group consisting of ketones, aldehydes, thioketones, thioaldehydes, imines and hydrazones; and a silyl cyanide, e.g., trimethylsilyl cyanide. In preferred embodiments, the substrate is a ketone or aldehyde. A preferred embodiment of the present invention relates to practicing the method in a halocarbon solvent, e.g., chloroform. Another preferred embodiment of the present invention relates to practicing the method in an ester solvent, e.g., ethyl acetate. In certain embodiments, the methods of the present invention produce a silyl cyanohydrin with an enantiomeric excess greater than about 80%. In certain embodiments, the methods of the present invention produce a silyl cyanohydrin with an enantiomeric excess greater than about 90%.

37 Claims, 21 Drawing Sheets

(DHQ)₂PHAL         (DHQD)₂PHAL (DHQ)₂PYR          (DHQD)₂PYR (DHQ)₂AQN          (DHQD)₂AQN

OTHER PUBLICATIONS

Choi et al.; "Catalytic Asymmetric Synthesis of (S)-Acetophenone Cyanohydrin Under High Pressure", Tetrahedron Letters, 38(38): 6669-6672, (1997).

Deng et al.; "Aluminum-Catalyzed Asymmetric Addition of TMSCN to Aromatic and Aliphatic Ketones Promoted by an Easily Accessible and Recyclable Peptide Ligand", Angew. Chem. Int. Ed. 41(6): 1009-1012, (2002).

Hamashima et al.; "Catalytic Enantioselective Cyanosilylation of Ketones: Improvement of Enantioselectivity and Catalyst Turn-over by Ligand Tuning", Tetrahedron Letters 42: 691-694, (2001).

Hamashima et al.; "Catalytic Enantioselective Cyanosilylation of Ketones", J. Am. Chem. Soc. 122: 7412-7413, (2000).

Kanai et al.; "Design of a New Bifunctional Symmetric Catalyst from Carbohydrates: Application to Catalytic asymmetric Cyanosilylation of Aldehydes and Acetophenone", Tetrahdron Letters 41: 2405-2409, (2000).

Kanai Motomu; "Development and Application of Enantioselective Lewis Acid-Lewis Base Bifunctional Catalyst", Yakugaku Zasshi 121(12): 949-960, (2001).

Kiljunen et al.; "Approach to (R)- and (S) -Ketone Cyanohydrins Using almond and Apple Meal as the Source of (R) -Oxynitrilase", Tetrahedron Asymmetry 8(10): 1551-1557, (1997).

Kobayashi et al.; "Enantioselective Addition Rection of Trimethylsilyl Cyanide with Aldehydes Using a Chiral Tin (II) Lewis Acid", Chemistry Letters, pp. 541-544, (1991).

Kobayashi et al.; "A Facile Synthesis of Cyanohydrin Trimethylsilyl Ethers by the Addition Reaction of Trimethylsilyl Cyanide with Aldehydes Under Basic Condition", Chemistry Letters, pp. 537-540, (1991).

Masumoto et al.; "A Practical Synthesis of (S)-Oxybutynin", Tetrahedron Letters, 43: 8647-8651, (2002).

Masumoto et al.; "Practical Synthesis of Chiral Ligands for Catalytic Enantioselective Cyanosilylation of Ketones", Tetrahedron Letters 43: 2919-2922, (2002).

Yabu et al.; "Catalytic Enantioselective Synthesis of (20s)-Camptothecin Intermediates Using Cyanosilylation of Ketones Promoted by D-Glucose-Derived Lanthanide Catalyst", Heterocycles, 59(1): 369-385, (2003).

Yabu et al.; "Switching Enantiofacial Selectivities Using One Chiral Source: Catalytic Enantioselective Synthesis of the Key Intermediate for (20s)-Camptothecin Family by (S) -Selective Cyanosilation of Ketones", J. Am. Chem. Soc. 123: 9908-9909, (2001).

Yabu et al.; "Studies Toward Practical Synthesis of (20S) - Camptothecin Family Through Catalytic Enantioselective Cyanosilylation of Ketones: Improved Catalyst Efficiency by Ligand-tuning", Tetrahedron Letters 43: 2923-2926, (2002).

Figure 2
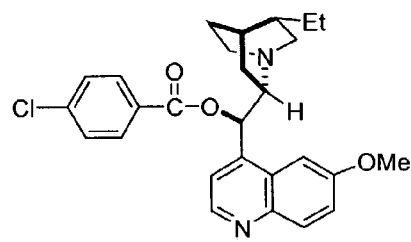
DHQ-CLB
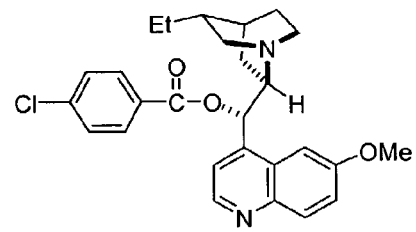
DHQD-CLB
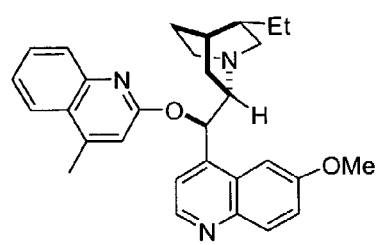
DHQ-MEQ
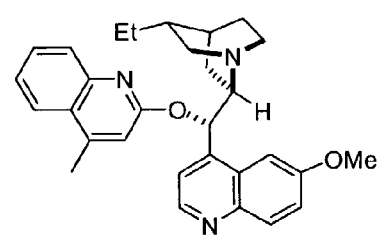
DHQD-MEQ
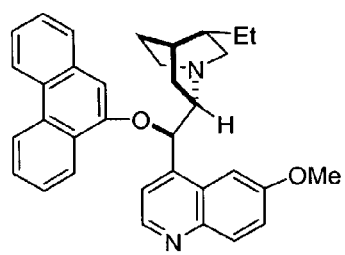
DHQ-AQN
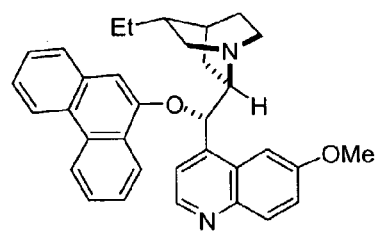
DHQD-AQN
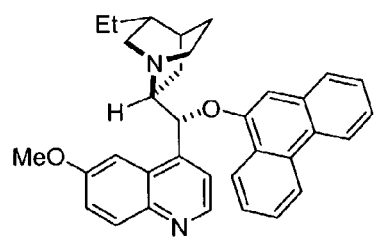
DHQ-PHN
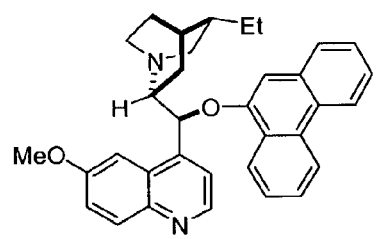
DHQD-PHN

Figure 3

| Starting Material | Catalyst | T (°C) | Time (h) | Yield (%) | Ee (%) |
|---|---|---|---|---|---|
| CH₃-C(O)-CH(OPr)(OPr) | (DHQ)₂AQN (2 mol%) | -50 | 46 | 97 | 92 |
| | DHQD-PHN (30 mol%) | -50 | 91 | 96 | 91 |
| Ph-CH₂-CH₂-C(O)-CH(OPr)(OPr) | (DHQ)₂AQN (20 mol%) | -50 | 24 | 96 | 97 |
| n-Bu-C(O)-CH(OEt)(OEt) | (DHQ)₂AQN (5 mol%) | -50 | 18 | 92 | 90 |
| Ph-CH=CH-C(O)-CH(OPr)(OPr) | (DHQ)₂AQN (2 mol%) | -50 | 16 | 93 | 91 |
| 4-MeO-C₆H₄-CH=CH-C(O)-CH(OPr)(OPr) | (DHQ)₂AQN (2 mol%) | -50 | 18 | 92 | 90 |
| 4-Cl-C₆H₄-CH=CH-C(O)-CH(OPr)(OPr) | (DHQ)₂AQN (2 mol%) | -50 | 18 | 95 | 92 |
| 3-pyridyl-CH=CH-C(O)-CH(OPr)(OPr) | (DHQ)₂AQN (2 mol%) | -50 | 18 | 97 | 93 |

Figure 4
| Starting Material | Catalyst | T (°C) | Time (h) | Yield (%) | Ee (%) |
|---|---|---|---|---|---|
| 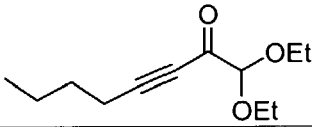 | (DHQ)$_2$AQN (2 mol%) | -50 | 18 | 94 | 95 |
| 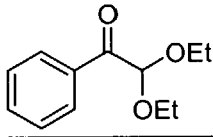 | (DHQ)$_2$AQN (2 mol%) | -50 | 19 | 98 | 90 |
| 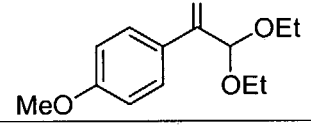 | (DHQ)$_2$AQN (2 mol%) | -50 | 18 | 94 | 97 |
| 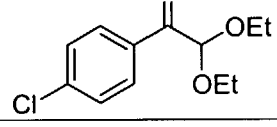 | (DHQ)$_2$AQN (2 mol%) | -50 | 18 | 96 | 98 |
| 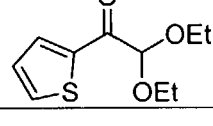 | (DHQ)$_2$AQN (2 mol%) | -50 | 18 | 97 | 87 |
| 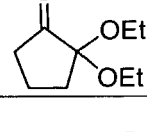 | DHQD-PHN (35 mol%) | -60 | 99 | 72 | 90 |
| 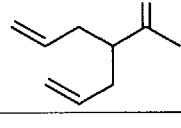 | (DHQ)$_2$AQN (35 mol%) | -60 | 94 | 90 | 81 |

Figure 5

| Starting Material | Catalyst | Solvent | T (°C) | Time (h) | Yield (%) | Ee (%) |
|---|---|---|---|---|---|---|
| CH₃C(O)CH(OPr)₂ | (DHQ)₂AQN (2 mol%) | CHCl₃ | -50 | 46 | 97 | 92 |
| | (DHQD)₂PHAL (5 mol%) | EtOAc | -24 | 24 | 96 | -92 |
| PhCH₂CH₂C(O)CH(OPr)₂ | (DHQ)₂AQN (20 mol%) | CHCl₃ | -50 | 24 | 96 | 97 |
| n-BuC(O)CH(OEt)₂ | (DHQ)₂AQN (5 mol%) | CHCl₃ | -50 | 18 | 92 | 90 |
| i-PrC(O)CH(OEt)₂ | (DHQ)₂AQN (20 mol%) | CHCl₃ | -40 | 94 | 81 | 94 |
| cyclopentyl-C(O)CH(OEt)₂ | (DHQ)₂AQN (20 mol%) | CHCl₃ | -50 | 89 | 76 | 88 |
| cyclohexyl-C(O)CH(OEt)₂ | (DHQ)₂AQN (20 mol%) | CHCl₃ | -50 | 89 | 69 | 90 |
| PhCH=CHC(O)CH(OPr)₂ | (DHQ)₂AQN (2 mol%) | CHCl₃ | -50 | 16 | 93 | 91 |
| 4-MeO-C₆H₄-CH=CHC(O)CH(OPr)₂ | (DHQ)₂AQN (2 mol%) | CHCl₃ | -50 | 18 | 92 | 90 |
| | (DHQD)₂PHAL (10 mol%) | EtOAc | -30 | 21 | 96 | -92 |

Figure 6

| Starting Material | Catalyst | Solvent | T (°C) | Time (h) | Yield (%) | Ee (%) |
|---|---|---|---|---|---|---|
| 4-Cl-C6H4-CH=CH-C(O)-CH(OPr)2 | (DHQ)2AQN (2 mol%) | CHCl3 | -50 | 18 | 95 | 92 |
| 3-pyridyl-CH=CH-C(O)-CH(OPr)2 | (DHQ)2AQN (2 mol%) | CHCl3 | -50 | 18 | 97 | 93 |
| Bu-C≡C-C(O)-CH(OEt)2 | (DHQ)2AQN (2 mol%) | CHCl3 | -50 | 18 | 94 | 95 |
| Ph-C≡C-C(O)-CH(OEt)2 | (DHQ)2AQN (2 mol%) | CHCl3 | -50 | 19 | 93 | 96 |
|  | (DHQD)2PHAL (10 mol%) | EtOAc | -30 | 21 | 96 | -93 |
| Ph-C(O)-CH(OEt)2 | (DHQ)2AQN (2 mol%) | CHCl3 | -50 | 19 | 98 | 90 |

Figure 7
| Starting Material | Catalyst | Solvent | T (°C) | Time (h) | Yield (%) | Ee (%) |
|---|---|---|---|---|---|---|
| 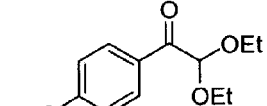 | (DHQ)₂AQN (2 mol%) | CHCl₃ | -50 | 18 | 94 | 97 |
| 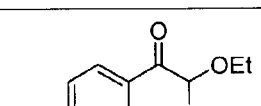 | (DHQ)₂AQN (2 mol%) | CHCl₃ | -50 | 18 | 96 | 98 |
|  | (DHQD)₂AQN (2 mol%) | CHCl₃ | -60 | 14 | 95 | -94 |
| 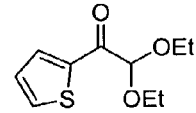 | (DHQ)₂AQN (2 mol%) | CHCl₃ | -60 | 36 | 97 | 87 |
| 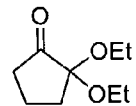 | DHQD-PHN (35 mol%) | CHCl₃ | -60 | 99 | 72 | 90 |
| 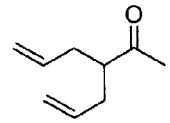 | (DHQ)₂AQN (35 mol%) | CHCl₃ | -60 | 94 | 90 | 81 |

| Catalyst | Solvent | Time (h) | Conversion (%) | Ee (%) |
|---|---|---|---|---|
| Quinine (Q) (10 mol%) | $CHCl_3$ | 4 | 98 | 4.1 |
| Quinidine (QD) (10 mol%) | $CHCl_3$ | 4 | 99 | -17 |
| DHQ-CLB (10 mol%) | $CHCl_3$ | 4 | | |
| | | 24 | | |
| DHQD-CLB (10 mol%) | $CHCl_3$ | 4 | 13 | -68 |
| | | 24 | 40 | -72 |
| DHQ-MEQ (10 mol%) | $CHCl_3$ | 4 | | |
| | | 24 | | |
| DHQD-MEQ (10 mol%) | $CHCl_3$ | 4 | 19 | -81 |
| | | 24 | 97 | -86 |
| DHQ-PHN (10 mol%) | $CHCl_3$ | 4 | 14 | 85 |
| | | 24 | 42 | 82 |

| Catalyst | Solvent | Time (h) | Conversion (%) | Ee (%) |
|---|---|---|---|---|
| DHQD-PHN (10 mol%) | CHCl$_3$ | 4 | 16 | -81 |
| | | 24 | 93 | -86 |
| (DHQ)$_2$PHAL (5 mol%) | CHCl$_3$ | 4 | 9.5 | 83 |
| | | 24 | 44 | 83 |
| (DHQD)$_2$PHAL (5 mol%) | CHCl$_3$ | 4 | 7.5 | -86 |
| | | 24 | 26 | -89 |
| (DHQ)$_2$PYR (5 mol%) | CHCl$_3$ | 4 | 9.4 | 74 |
| | | 24 | 43 | 75 |
| (DHQD)$_2$PYR (5 mol%) | CHCl$_3$ | 4 | 9.5 | -83 |
| | | 24 | 44 | -83 |
| (DHQ)$_2$AQN (5 mol%) | CHCl$_3$ | 4 | 99 | 89 |
| (DHQD)$_2$AQN (5 mol%) | CHCl$_3$ | 4 | 98 | -73 |

| Catalyst | Solvent | Time (h) | Conversion (%) | Ee (%) |
|---|---|---|---|---|
| (DHQ)₂AQN | CHCl₃ | 4 | 99 | 89 |
| (DHQ)₂AQN | CH₂Cl₂ | 4 | 77 | 85 |
|  |  | 24 | 99 | 85 |
| (DHQ)₂AQN | CCl₄ | 4 | 4.0 | -- |
|  |  | 24 | 20 | 83 |
| (DHQ)₂AQN | ClCH₂CH₂Cl | 4 | 42 | 84 |
|  |  | 24 | 100 | 88 |
| (DHQ)₂AQN | PhMe | 4 | 3.6 | -- |
|  |  | 24 | 18 | 83 |
| (DHQ)₂AQN | Et₂O | 4 | 18 | -- |
|  |  | 24 | 58 | 84 |
| (DHQ)₂AQN | THF | 4 | 88 | 74 |
|  |  | 24 | 100 | 74 |
| (DHQ)₂AQN | EtOAc | 4 | 99 | 83 |
| (DHQ)₂AQN | MeCN | 4 | 100 | 64 |
| (DHQ)₂AQN | DMF | 4 | 100 | 43 |

| Catalyst | Solvent | Time (h) | Conversion (%) | Ee (%) |
|---|---|---|---|---|
| DHQD-MEQ (10 mol%) | EtOAc | 4 | 51 | -84 |
|  |  | 24 | 98 | -85 |
| DHQ-PHN (10 mol%) | EtOAc | 4 | 78 | 74 |
|  |  | 24 | 99 | 74 |
| DHQD-PHN (10 mol%) | EtOAc | 4 | 78 | -81 |
|  |  | 24 | 99 | -82 |
| (DHQ)$_2$PHAL (5 mol%) | EtOAc | 4 | 11 | 65 |
|  |  | 24 | 48 | 66 |
| (DHQD)$_2$PHAL (5 mol%) | EtOAc | 4 | 52 | -91 |
|  |  | 24 | 99 | -92 |
| (DHQ)$_2$PYR (5 mol%) | EtOAc | 4 | 26 | 78 |
|  |  | 24 | 73 | 76 |
| (DHQD)$_2$PYR (5 mol%) | EtOAc | 4 | 13 | -86 |
|  |  | 24 | 43 | -85 |
| (DHQ)$_2$AQN (5 mol%) | EtOAc | 4 | 99 | 83 |
| (DHQD)$_2$AQN (5 mol%) | EtOAc | 4 | 99 | -74 |

| Solvent | Time/h | P/(P+S)% | ee% |
|---|---|---|---|
| CHCl₃ | 4 | 42 | 22 |
| | 22 | 71 | 17 |
| CH₂Cl₂ | 4 | 59 | 39 |
| | 22 | 94 | 33 |
| CCl₄ | 4 | 35 | 36 |
| | 22 | 82 | 31 |
| ClCH₂CH₂Cl | 4 | 57 | 43 |
| | 22 | 92 | 34 |
| Cl₂CHCHCl₂ | 4 | 27 | 23 |
| | 22 | 42 | 14 |
| hexanes | 4 | 47 | 30 |
| | 22 | 96 | 29 |
| PhMe | 4 | 25 | 33 |
| | 22 | 76 | 27 |
| Et₂O | 4 | 13 | 33 |
| | 22 | 63 | 33 |
| THF | 4 | 11 | 34 |
| | 22 | 45 | 31 |
| EtOAc | 4 | 19 | 32 |
| | 22 | 63 | 34 |
| MeCN | 4 | 50 | 26 |
| | 22 | 57 | 29 |
| none | 4 | 100 | 37 |

| Solvent | Time/h | P/(P+S)% | ee% |
|---|---|---|---|
| CHCl$_3$ | 21 | 35 | 13 |
| CH$_2$Cl$_2$ | 4 | 30 | 43 |
|  | 23 | 90 | 37 |
| CCl$_4$ | 21 | 11 | 35 |
| hexanes | 20 | 9.8 | 33 |
| PhMe | 20 | 8.0 | 37 |
| Et$_2$O | 21 | 1.6 | -- |
| THF | 21 | 11 | 43 |
| EtOAc | 23 | 2.1 | -- |
| MeCN | 23 | 32 | 37 |

| Catalyst | Time/h | P/(P+S)% | ee% |
|---|---|---|---|
| QD (20) | 21 | 96 | 2 |
| DHQD-CLB (20) | 21 | 50 | 0 |
| DHQD-MEQ (20) | 21 | 91 | 19 |
| DHQD-PHN (20) | 21 | 89 | 21 |
| DHQ-PHN (20) | 4 | 18 | 35 |
|  | 23 | 69 | 25 |
| (DHQD)$_2$PHAL (10) | 21 | 32 | 21 |
| (DHQD)$_2$PYR (10) | 21 | 85 | 28 |
| (DHQ)$_2$PYR (10) | 4 | 30 | 43 |
|  | 23 | 90 | 37 |
| (DHQD)$_2$AQN (10) | 21 | 97 | 18 |

Figure 15

| Ketone | Catalyst (mol%) | Temp (°C) | Time (h) | Yield (%) | ee % | Config. |
|---|---|---|---|---|---|---|
| 1a (CH₃-CO-CH(OPr-n)₂) | (DHQ)₂AQN (2)<br>(DHQD)₂PHAL (5) | -50<br>-50 | 46<br>88 | 97<br>95 | 92<br>96 | R-(-)<br>S-(+) |
| 1b (PhCH₂CH₂-CO-CH(OPr-n)₂) | (DHQ)₂AQN (20) | -50 | 24 | 96 | 97 | (+) |
| 1c (n-Bu-CO-CH(OEt)₂) | (DHQ)₂AQN (5) | -50 | 18 | 92 | 90 | (+) |
| 1d (iPr-CO-CH(OEt)₂) | (DHQ)₂AQN (20) | -40 | 94 | 81 | 94 | (+) |
| 1e (cyclopentyl-CO-CH(OEt)₂) | (DHQ)₂AQN (20) | -50 | 89 | 76 | 88 | (+) | a) Unless specified, the reaction was run in chloroform with 3.0 eq. of trimethylsilyl cyanide. b) The solvent was ethyl acetate. c) 2.0 eq. of trimethylsilyl cyanide were used.

Figure 16
| Ketone | Catalyst (mol%) | Temp (°C) | Time (h) | Yield (%) | ee % | Config. |
|---|---|---|---|---|---|---|
| 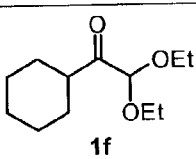 1f | (DHQ)₂AQN (20) | -50 | 89 | 69 | 90 | (+) |
| 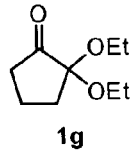 1g | (DHQD)₂PHAL (20) | -50 | 96 | 66 | 92 | (+) |
| 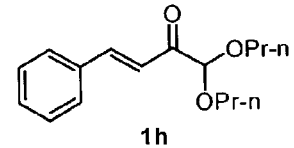 1h | (DHQ)₂AQN (2) | -50 | 16 | 93 | 91 | (+) |
| 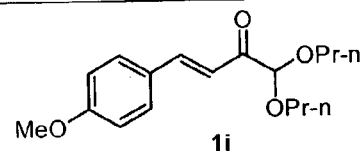 1i | (DHQ)₂AQN (2) (DHQD)₂PHAL (10) | -50 -30 | 18 21 | 92 96 | 90 92 | (+) (-) |
| 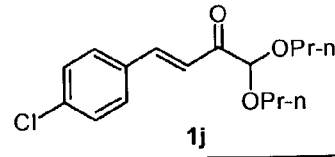 1j | (DHQ)₂AQN (2) | -50 | 18 | 95 | 92 | (+) |
| 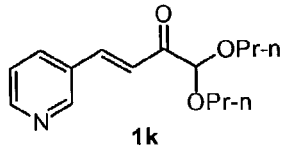 1k | (DHQ)₂AQN (2) | -50 | 18 | 97 | 93 | (+) |
a) Unless specified, the reaction was run in chloroform with 3.0 eq. of trimethylsilyl cyanide. b) The solvent was ethyl acetate. c) 2.0 eq. of trimethylsilyl cyanide were used.

Figure 17

| Ketone | Catalyst (mol%) | Temp (°C) | Time (h) | Yield (%) | ee % | Config. |
|---|---|---|---|---|---|---|
| 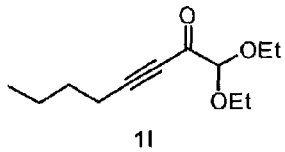 1l | (DHQ)₂AQN (2) | -50 | 18 | 94 | 95 | (+) |
| 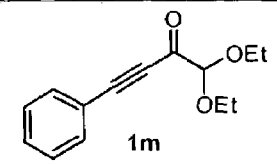 1m | (DHQ)₂AQN (2)<br>(DHQD)₂PHAL (10) | -50<br>-30 | 19<br>21 | 93<br>96 | 96<br>93 | (+)<br>(-) |
| 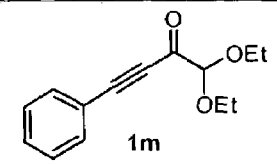 1n | (DHQ)₂AQN (2) | -50 | 19 | 98 | 90 | (+) |
| 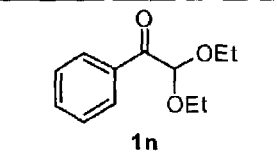 1o | (DHQ)₂AQN (2) | -50 | 18 | 94 | 97 | (+) |
| 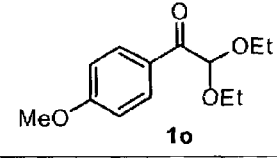 1p | (DHQ)₂AQN (2)<br>(DHQD)₂AQN (2)<br>(DHQD)₂PHAL (10) | -50<br>-60<br>-50 | 18<br>14<br>40 | 96<br>95<br>99 | 98<br>94<br>94 | (+)<br>(-)<br>(-) |
| 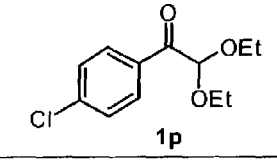 1q | (DHQ)₂AQN (2) | -60 | 36 | 97 | 87 | (+) | a) Unless specified, the reaction was run in chloroform with 3.0 eq. of trimethylsilyl cyanide. b) The solvent was ethyl acetate. c) 2.0 eq. of trimethylsilyl cyanide were used.

Figure 18
| Ketone | TMSCN (eq.) | Catalyst (mol%) | Temp (°C) | Time (h) | P/(P+S) (%)[c] | ee% |
|---|---|---|---|---|---|---|
| 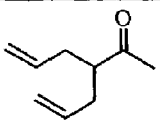 | 3.0 | (DHQ)₂PYR (10) | -24 | 19 | 56 | 65 |
| | | | | 43 | 89 | 63 |
| | 3.0 | (DHQ)₂AQN (10) | -24 | 17 | 94 | 60 |
| | 4.0 | (DHQ)₂PYR (35) | -60 | 96 | 76 | 80 |
| | 3.0 | (DHQ)₂AQN (10) | -24 | 16 | 98 | 59 |
| | 5.0 | (DHQ)₂AQN (10) | -24 | 5 | 67 | 60 |
| | 5.0 | (DHQ)₂AQN (10) | -24 | 2 | 81 | 58 |
| | 4.0 | DHQ-PHN (20) | -24 | 4 | 18 | 49 |
| | 4.0 | (DHQ)₂AQN (15) | -50 | 92 | 99 | 74 |
| | 4.0 | (DHQ)₂AQN (25) | -60 | 84 | 77 | 80 |
| | 4.0 | (DHQ)₂AQN (35) | -60 | 94 | 95 (90) | 81 |
| 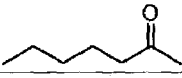 | 4.0 | (DHQ)₂AQN (10) | -60 | 12 | 32 | 48 |
| 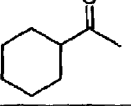 | 4.0 | (DHQ)₂AQN (25) | -60 | 84 | 96 | 76 |
| 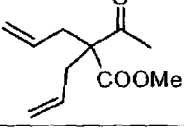 | 3.0 | (DHQ)₂AQN (10) | -24 | 38 | 60 | 55 |
|  | 4.0 | (DHQ)₂AQN (15) | -50 | 94 | 84 (68) | 61 |
| | 4.0 | (DHQ)₂AQN (35) | -60 | 94 | 92 (87) | 68 |
a) Unless specified, the reaction was run with 0.20 mmol of ketone in 0.20 mL of chloroform. b) The solvent was dichloromethane. c) The isolated yield is in parentheses.

Figure 19

| Ketone | TMSCN (eq.) | Catalyst (mol%) | Temp (°C) | Time (h) | P/(P+S) (%)[c] | ee% |
|---|---|---|---|---|---|---|
| (2,2-dimethylcyclohexanone) | 4.0 | (DHQ)₂AQN (15) | -50 | 94 | 88 (81) | 43 |
|  | 4.0 | (DHQ)₂AQN (35) | -60 | 94 | 81 (71) | 55 |
| (dimethylcyclopentenone) | 4.0 | (DHQ)₂AQN (35) | -24 | 20 | 17 | 69 |
|  | 4.0 | DHQD-PHN (50) | -24 | 20 | 3.2 | 50 |
|  | 4.0 | (DHQ)₂PYR (30) | -24 | 19 | 3.6 | 81 |
| (cyclohexenone) | 4.0 | (DHQ)₂PYR (10) | -24 | 4 | 9.1 | 14 |
| (acetophenone) | 4.0 | (DHQ)₂AQN (10) | -24 | 16 | 91 | 31 |
|  | 4.0 | (DHQ)₂AQN (15) | -60 | 12 | 11 | 46 |
|  | 4.0 | (DHQ)₂PYR (10) | -24 | 48 | 99 | 39 |
|  | 4.0 | (DHQ)₂PYR (30) | -24 | 20 | 98 | 39 |
|  | 4.0 | DHQ-PHN (20) | -24 | 5 | 14 | 23 |
| (2'-iodoacetophenone) | 4.0 | (DHQ)₂PYR (10) | -24 | 18 | 47 | 19 |
| (1-indanone) | 4.0 | (DHQ)₂AQN (10) | -24 | 17 | 75 | 21 | a) Unless specified, the reaction was run with 0.20 mmol of ketone in 0.20 mL of chloroform. b) The solvent was dichloromethane. c) The isolated yield is in parentheses.

Figure 20

| Ketone | TMSCN (eq.) | Catalyst (mol%) | Temp (°C) | Time (h) | P/(P+S) (%)[c] | ee% |
|---|---|---|---|---|---|---|
| PhC(O)CHCl₂ | 4.0 | (DHQ)₂AQN (10) | -24 | 7 | 100 | 14 |
| PhC(O)CH(OEt)₂ | 4.0 | (DHQ)₂AQN (10) | -24 | 7 | 100 | 74 |
|  | 4.0 | (DHQ)₂AQN (35) | -70 | 37 | 100 (94) | 78 |
|  | 3.0 | DHQD-PHN (35) | -50 | 46 | 99 (98) | 58 |
|  | 3.0 | DHQ-PHN (35) | -50 | 46 | 99 (95) | 63 |
| PhC(O)CH(OC₈H₁₇-n)₂ | 4.0 | (DHQ)₂AQN (10) | -24 | 8 | 100 (99) | 73 |
| PhC(O)CH(OAll)₂ | 4.0 | (DHQ)₂AQN (10) | -24 | 8 | 100 (100) | 64 |
| PhC(O)CH(OCy)₂ | 4.0 | (DHQ)₂AQN (10) | -24 | 7 | 100 (98) | 57 |
| MeC(O)C(Me)(OEt)₂ | 4.0 | (DHQ)₂AQN (15) | -50 | 96 | 73 (63) | 10 |
|  | 3.0 | DHQD-PHN (35) | -50 | 144 | 88 (76) | 54 | a) Unless specified, the reaction was run with 0.20 mmol of ketone in 0.20 mL of chloroform. b) The solvent was dichloromethane. c) The isolated yield is in parentheses.

Figure 21

| Ketone | TMSCN (eq.) | Catalyst (mol%) | Temp (°C) | Time (h) | P/(P+S) (%)[c] | ee% |
|---|---|---|---|---|---|---|
| 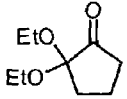 | 4.0<br>3.0<br>3.0<br>3.0 | (DHQ)₂AQN (15)<br>DHQD-PHN (35)<br>DHQD-PHN (35)<br>DHQ-PHN (35) | -50<br>-50<br>-60<br>-60 | 20<br>89<br>99<br>168 | 100 (95)<br>98<br>81(72)<br>66 (60) | 66<br>89<br>90<br>84 |
| 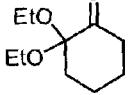 | 4.0<br>3.0 | (DHQ)₂AQN (15)<br>DHQD-PHN (35) | -50<br>-50 | 96<br>144 | 87 (78)<br>33 (28) | 57<br>81 |
| 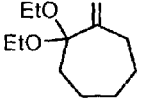 | 4.0 | (DHQ)₂AQN (15) | -24 | 75 | 12 | -- |
| 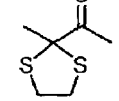 | 4.0 | (DHQ)₂AQN (35) | -40 | 28 | 98 (92) | 57 |
|  | 4.0 | (DHQ)₂AQN (10) | -60 | 22 | 100 | 51 |
|  | 4.0 | (DHQ)₂AQN (10) | -60 | 21 | 100 | 43 | a) Unless specified, the reaction was run with 0.20 mmol of ketone in 0.20 mL of chloroform. b) The solvent was dichloromethane. c) The isolated yield is in parentheses.

1

CATALYTIC ASYMMETRIC CYANOSILYLATION OF KETONES, ALDEHYDES, THIOKETONES, THIOALDEHYDES, IMINES AND HYDRAZONES

RELATED APPLICATIONS

This application claims the benefit of priority to U.S. Provisional Application for Patent Ser. No. 60/356,993, filed Feb. 13, 2002.

GOVERNMENT SUPPORT

The invention was made with support provided by the National Institutes of Health (Grant No. R01 GM-61591); therefore, the government has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sep. 28, 1992, pp. 46–79) include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming. Furthermore, resolution often means that the undesired enantiomer is discarded, thus decreasing efficiency and wasting half of the material.

SUMMARY OF THE INVENTION

One aspect of the present invention relates to a method for the catalytic asymmetric cyanosilylation of ketones, aldehydes, thioketones, thioaldehydes, imines and hydrazones. The critical elements of the method are: a non-racemic chiral tertiary-amine-containing catalyst; a substrate selected from the group consisting of ketones, aldehydes, thioketones, thioaldehydes, imines and hydrazones; and a silyl cyanide, e.g., trimethylsilyl cyanide. In preferred embodiments, the substrate is a ketone or aldehyde. A preferred embodiment of the present invention relates to practicing the method in a halocarbon solvent, e.g., chloroform. Another preferred embodiment of the present invention relates to practicing the method in an ester solvent, e.g., ethyl acetate. In certain embodiments, the methods of the present invention produce a silyl cyanohydrin with an enantiomeric excess greater than about 80%. In certain embodiments, the methods of the present invention produce a silyl cyanohydrin with an enantiomeric excess greater than about 90%.

BRIEF DESCRIPTION OF THE DRAWINGS

FIG. 2 depicts the structures of certain catalysts used in the methods of the present invention, and their abbreviations herein.

FIG. 3 tabulates the results of catalytic asymmetric cyanosilylations of various ketones according to the methods of the present invention.

FIG. 4 tabulates the results of catalytic asymmetric cyanosilylations of various ketones according to the methods of the present invention.

FIG. 5 tabulates the results of catalytic asymmetric cyanosilylations of various ketones according to the methods of the present invention.

FIG. 6 tabulates the results of catalytic asymmetric cyanosilylations of various ketones according to the methods of the present invention.

FIG. 7 tabulates the results of catalytic asymmetric cyanosilylations of various ketones according to the methods of the present invention.

FIG. 15 tabulates the results of the catalytic asymmetric cyanosilylation of various alpha,alpha-dialkoxy ketones according to the methods of the present invention.

FIG. 16 tabulates the results of the catalytic asymmetric cyanosilylation of various alpha,alpha-dialkoxy ketones according to the methods of the present invention.

FIG. 17 tabulates the results of the catalytic asymmetric cyanosilylation of various alpha,alpha-dialkoxy ketones according to the methods of the present invention.

FIG. 18 tabulates the results of the catalytic asymmetric cyanosilylation of various substrates according to the methods of the present invention.

FIG. 19 tabulates the results of the catalytic asymmetric cyanosilylation of various substrates according to the methods of the present invention.

FIG. 20 tabulates the results of the catalytic asymmetric cyanosilylation of various substrates according to the methods of the present invention.

FIG. 21 tabulates the results of the catalytic asymmetric cyanosilylation of various substrates according to the methods of the present invention.

DETAILED DESCRIPTION OF THE INVENTION

Figure 1:
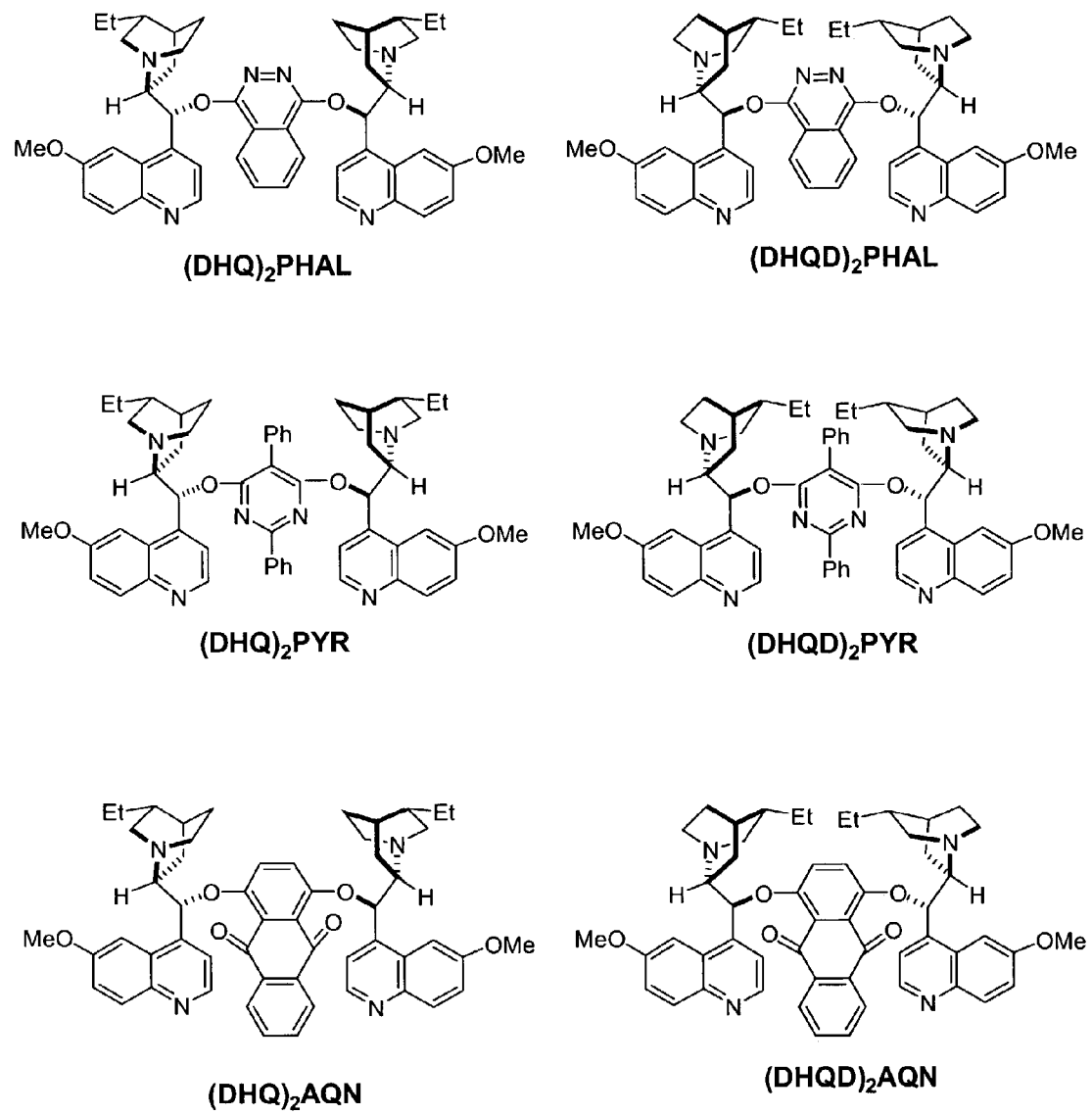
FIG. 1 depicts the structures of certain catalysts used in the methods of the present invention, and their abbreviations herein.
Figure 8:
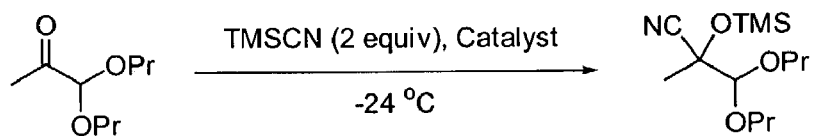
FIG. 8 tabulates the results of the catalytic asymmetric cyanosilylation of a ketone in chloroform according to the methods of the present invention as a function of the catalyst used.
Figure 9:
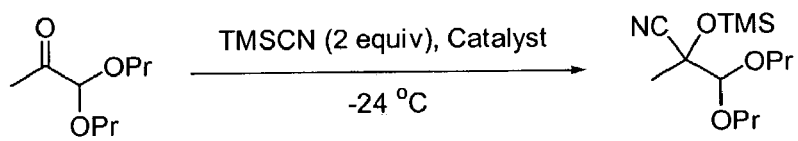
FIG. 9 tabulates the results of the catalytic asymmetric cyanosilylation of a ketone in chloroform according to the methods of the present invention as a function of the catalyst used.
Figure 10:
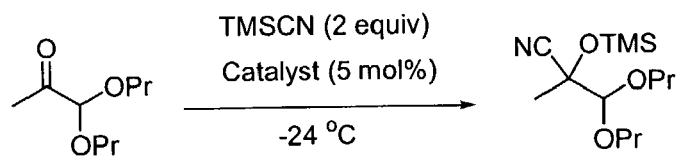
FIG. 10 tabulates the results of the catalytic asymmetric cyanosilylation of a ketone according to the methods of the present invention as a function of the solvent used.
Figure 11:
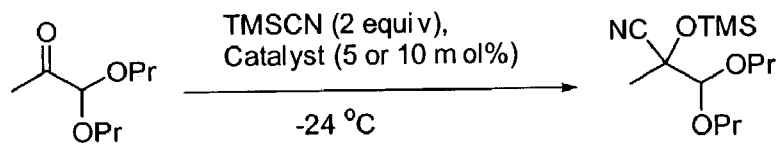
FIG. 11 tabulates the results of the catalytic asymmetric cyanosilylation of a ketone in ethyl acetate according to the methods of the present invention as a function of the catalyst used.

The ability to transform selectively an achiral or chiral compound comprising a prochiral center to an enantiomerically- or diastereomerically-enriched or an enantiomerically- or diastereomerically-pure chiral compound has broad applicability in the art of organic chemistry, especially in the agricultural and pharmaceutical industries, as well as in the polymer industry.

As described herein, the present invention relates to a method for the catalytic asymmetric cyanosilylation of ketones, aldehydes, thioketones, thioaldehydes, imines and hydrazones. The critical elements of the method are: a non-racemic chiral tertiary-amine-containing catalyst; a substrate ketone, aldehyde, thioketone, thioaldehyde, imine or hydrazone; and a silyl cyanide, e.g., trimethylsilyl cyanide. In preferred embodiments, the substrate is a ketone or aldehyde.

In the methods of the present invention, said silyl cyanide selectively reacts with one of the diastereomeric transition states or intermediates or both formed from the catalyst and substrate, generating an enantiomerically- or diastereomerically-enriched or an enantiomerically- or diastereomerically-pure chiral product. Moreover, the yields of the asymmetric cyanosilylations exceed 50% because the initial interactions between the substrate and the catalysts are reversible.

A preferred embodiment of the present invention relates to practicing the method in a halocarbon solvent, e.g., chloroform. Another preferred embodiment of the present invention relates to practicing the method in an ester solvent, e.g., ethyl acetate. In certain embodiments, the methods of the present invention produce a silyl cyanohydrin with an enantiomeric excess greater than about 80%. In certain embodiments, the methods of the present invention produce a silyl cyanohydrin with an enantiomeric excess greater than about 90%.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate that is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% enantiomeric excess (ee) A=(% enantiomer A)−
(% enantiomer B)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

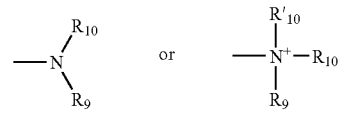

wherein $R_9$, $R_{10}$ and $R'_{10}$ each independently represent a group permitted by the rules of valence.

The term "acylamino" is art-recognized and refers to a moiety that can be represented by the general formula:

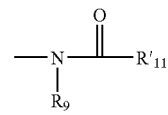

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

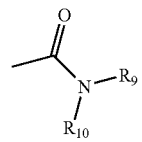

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

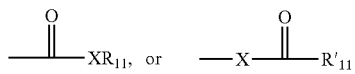

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

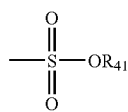

in which $R_{41}$ is an electron pair, hydrogen, alkyl, cycloalkyl, or aryl.

the term "sulfate" is art recognized and includes a moiety that can be represented by the general formula:

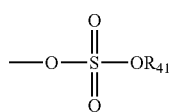

in which $R_{41}$ is as defined above.

The term "sulfonylamino" is art recognized and includes a moiety that can be represented by the general formula:

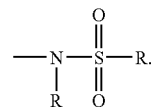

The term "sulfamoyl" is art-recognized and includes a moiety that can be represented by the general formula:

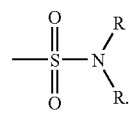

The term "sulfonyl", as used herein, refers to a moiety that can be represented by the general formula:

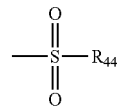

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

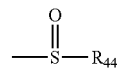

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986–87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled Standard List of Abbreviations. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2$^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Catalysts of the Invention

The catalysts employed in the subject methods are non-racemic chiral tertiary amines, phosphines and arsines which present an asymmetric environment, and form diastereomeric transition states or intermediates or both with the substrate. The diastereomeric transition states or intermediates then react at different rates with the silyl cyanide reagent to give a catalytic asymmetric transformation. In preferred embodiments, catalysts employed in the subject methods are non-racemic chiral tertiary amines, e.g., cinchona alkaloids. In general, catalysts useful in the methods of the present invention can be characterized in terms of a number of features. For instance, in preferred embodiments, the catalysts comprise asymmetric bicyclic or polycyclic scaffolds incorporating a tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states or intermediates for the overall transformation. Furthermore, the choice of substituents on the tertiary amine may also effect catalyst reactivity; in general, bulkier substituents are found to provide higher catalyst turnover numbers.

A preferred embodiment for each of the embodiments described above provides a catalyst having a molecular weight less than 2,000 g/mol, more preferably less than 1,000 g/mol, and even more preferably less than 500 g/mol. Additionally, the substituents on the catalyst can be selected to influence the solubility of the catalyst in a particular solvent system. FIGS. 1 and 2 depict preferred embodiments of tertiary amine catalysts used in the methods of the present invention.

As mentioned briefly above, the choice of catalyst substituents can also effect the electronic properties of the catalyst. Substitution of the catalyst with electron-rich (electron-donating) moieties (including, for example, alkoxy or amino groups) may increase the electron density of the catalyst at the tertiary amine nitrogen, rendering it a stronger Bronsted and/or Lewis base. Conversely, substitution of the catalyst with electron-poor moieties (for example, chloro or trifluoromethyl groups) can result in lower electron density of the catalyst at the tertiary amine nitrogen, rendering it a weaker Bronsted and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

Methods of the Invention—Catalyzed Reactions

One aspect of the present invention relates to a method for the catalytic asymmetric cyanosilylation of ketones, aldehydes, thioketones, thioaldehydes, imines and hydrazones. The critical elements of the method are: a non-racemic chiral tertiary-amine-containing catalyst; a substrate ketone, aldehyde, thioketone, thioaldehyde, imine or hydrazone; and a silyl cyanide, e.g., trimethylsilyl cyanide. In preferred embodiments, the substrate is a ketone or aldehyde.

One aspect of the present invention relates to a method for the catalytic asymmetric cyanosilylation of ketones. The critical elements of the method are: a non-racemic chiral tertiary-amine-containing catalyst; a ketone; and a silyl cyanide, e.g., trimethylsilyl cyanide. A preferred embodiment of the present invention relates to practicing the method in a halocarbon solvent, e.g., chloroform. Another preferred embodiment of the present invention relates to practicing the method in an ester solvent, e.g., ethyl acetate. In certain embodiments, the methods of the present invention achieve asymmetric cyanosilylation of ketones with an overall yield in excess of 50%, preferably greater than 70%, and most preferably greater than 90%.

The method of this invention can provide optically active products with very high stereoselectivity, e.g., enantioselectivity or diastereoselectivity. In preferred embodiments of the subject cyanosilylations, the enantiomeric excess of the product is preferably greater than 50%, more preferably greater than 75% and most preferably greater than 90%. The processes of this invention can also be carried out under reaction conditions suitable for commercial use, and typically proceed at reaction rates suitable for large-scale operations.

Further, the chiral products made available by the methods of this invention can undergo further reaction(s) to afford desired derivatives thereof. Such permissible derivatization reactions can be carried out in accordance with conventional procedures known in the art. For example, potential derivatization reactions include esterification, N-alkylation of amides, and the like. The invention expressly contemplates the preparation of end-products and synthetic intermediates which are useful for the preparation or development or both of pharmaceuticals, e.g., cardiovascular drugs, non-steroidal anti-inflammatory drugs, central nervous system agents, and antihistaminics.

In certain embodiments, the present invention relates to a method of cyanosilylation of a substrate, comprising the step of combining a silyl cyanide, a substrate selected from the group consisting of ketones, aldehydes, thioketones, thioaldehydes, imines and hydrazones, and a chiral non-racemic catalyst, wherein said chiral non-racemic catalyst catalyzes the addition of said silyl cyanide to said substrate to give a chiral non-racemic silyl cyanohydrin.

In certain embodiments, the present invention relates to the aforementioned method, wherein said substrate is a ketone or aldehyde.

In certain embodiments, the present invention relates to the aforementioned method, wherein said silyl cyanide is a trialkylsilyl cyanide.

In certain embodiments, the present invention relates to the aforementioned method, wherein said silyl cyanide is trimethylsilyl cyanide.

In certain embodiments, the present invention relates to the aforementioned method, wherein said chiral non-racemic catalyst is a tertiary amine, phosphine or arsine.

In certain embodiments, the present invention relates to the aforementioned method, wherein said chiral non-racemic catalyst is a tertiary amine.

In certain embodiments, the present invention relates to the aforementioned method, wherein said chiral non-racemic catalyst is a cinchona alkaloid.

In certain embodiments, the present invention relates to the aforementioned method, wherein said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments, the present invention relates to the aforementioned method, wherein said substrate is a ketone or aldehyde; and said silyl cyanide is a trialkylsilyl cyanide.

In certain embodiments, the present invention relates to the aforementioned method, wherein said substrate is a ketone or aldehyde; said silyl cyanide is a trialkylsilyl cyanide; and said chiral non-racemic catalyst is a tertiary amine, phosphine or arsine.

In certain embodiments, the present invention relates to the aforementioned method, wherein said substrate is a ketone or aldehyde; said silyl cyanide is a trialkylsilyl cyanide; and said chiral non-racemic catalyst is a tertiary amine.

In certain embodiments, the present invention relates to the aforementioned method, wherein said substrate is a ketone or aldehyde; said silyl cyanide is a trialkylsilyl cyanide; and said chiral non-racemic catalyst is a cinchona alkaloid.

In certain embodiments, the present invention relates to the aforementioned method, wherein said substrate is a ketone or aldehyde; said silyl cyanide is a trialkylsilyl cyanide; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments, the present invention relates to the aforementioned method, wherein said substrate is a ketone or aldehyde; said silyl cyanide is trimethylsilyl cyanide; and said chiral non-racemic catalyst is a tertiary amine, phosphine or arsine.

In certain embodiments, the present invention relates to the aforementioned method, wherein said substrate is a ketone or aldehyde; said silyl cyanide is trimethylsilyl cyanide; and said chiral non-racemic catalyst is a tertiary amine.

In certain embodiments, the present invention relates to the aforementioned method, wherein said substrate is a ketone or aldehyde; said silyl cyanide is trimethylsilyl cyanide; and said chiral non-racemic catalyst is a cinchona alkaloid.

In certain embodiments, the present invention relates to the aforementioned method, wherein said substrate is a ketone or aldehyde; said silyl cyanide is trimethylsilyl cyanide; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments, the present invention relates to the aforementioned method, wherein the enantiomeric excess or diastereomeric excess of the chiral non-racemic silyl cyanohydrin is greater than about 50%.

In certain embodiments, the present invention relates to the aforementioned method, wherein the enantiomeric excess or diastereomeric excess of the chiral non-racemic silyl cyanohydrin is greater than about 70%.

In certain embodiments, the present invention relates to the aforementioned method, wherein the enantiomeric excess or diastereomeric excess of the chiral non-racemic silyl cyanohydrin is greater than about 90%.

In certain embodiments, the present invention relates to a method of asymmetric cyanosilylation represented by Scheme 1:

Scheme 1

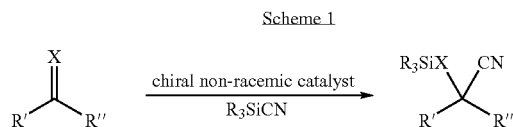

wherein

X represents O, S, NR', or NN(R')(R");

R represents independently for each occurrence alkyl, cycloalkyl, aryl, heteroaryl, aralkyl, or heteroaralkyl;

R' represents independently for each occurrence alkyl, cycloalkyl, alkenyl, alkynyl, aryl, heteroaryl, aralkyl, or heteroaralkyl;

R" represents independently for each occurrence H, alkyl, cycloalkyl, alkenyl, alkynyl, aryl, heteroaryl, aralkyl, or heteroaralkyl;

R' and R" are not identical;

the product is chiral and non-racemic; and chiral non-racemic catalyst is a chiral non-racemic tertiary amine, phosphine, or arsine.

In certain embodiments, the method of the present invention is represented by Scheme 1 and the attendant definitions, wherein X represents O.

In certain embodiments, the method of the present invention is represented by Scheme 1 and the attendant definitions, wherein R represents independently for each occurrence alkyl.

In certain embodiments, the method of the present invention is represented by Scheme 1 and the attendant definitions, wherein R represents independently for each occurrence methyl.

In certain embodiments, the method of the present invention is represented by Scheme 1 and the attendant definitions, wherein said chiral non-racemic catalyst is a chiral non-racemic tertiary amine.

In certain embodiments, the method of the present invention is represented by Scheme 1 and the attendant definitions, wherein said chiral non-racemic catalyst is a cinchona alkaloid.

In certain embodiments, the method of the present invention is represented by Scheme 1 and the attendant definitions, wherein said chiral non-racemic catalyst is quinidine, (DHQ)$_2$PHAL, (DHQD)$_2$PHAL, (DHQ)$_2$PYR, (DHQD)$_2$PYR, (DHQ)$_2$AQN,(DHQD)$_2$AQN, DHQ-CLB, DHQD-CLB, DHQ-MEQ, DHQD-MEQ, DHQ-AQN, DHQD-AQN, DHQ-PHN, or DHQD-PHN.

In certain embodiments, the method of the present invention is represented by Scheme 1 and the attendant definitions, wherein X represents O; and R represents independently for each occurrence alkyl.

In certain embodiments, the method of the present invention is represented by Scheme 1 and the attendant definitions, wherein X represents O; R represents independently for each occurrence alkyl; and said chiral non-racemic catalyst is a chiral non-racemic tertiary amine.

In certain embodiments, the method of the present invention is represented by Scheme 1 and the attendant definitions, wherein X represents O; R represents independently for each occurrence alkyl; and said chiral non-racemic catalyst is a cinchona alkaloid.

In certain embodiments, the method of the present invention is represented by Scheme 1 and the attendant definitions, wherein X represents O; R represents independently for each occurrence alkyl; and said chiral non-racemic catalyst is quinidine, (DHQ)$_2$PHAL, (DHQD)$_2$PHAL, (DHQ)$_2$PYR, (DHQD)$_2$PYR, (DHQ)$_2$AQN, (DHQD)$_2$AQN, DHQ-CLB, DHQD-CLB, DHQ-MEQ, DHQD-MEQ, DHQ-AQN, DHQD-AQN, DHQ-PHN, or DHQD-PHN.

In certain embodiments, the method of the present invention is represented by Scheme 1 and the attendant definitions, wherein X represents O; and R represents independently for each occurrence methyl.

In certain embodiments, the method of the present invention is represented by Scheme 1 and the attendant definitions, wherein X represents O; R represents independently for each occurrence methyl; and said chiral non-racemic catalyst is a chiral non-racemic tertiary amine.

In certain embodiments, the method of the present invention is represented by Scheme 1 and the attendant definitions, wherein X represents O; R represents independently for each occurrence methyl; and said chiral non-racemic catalyst is a cinchona alkaloid.

In certain embodiments, the method of the present invention is represented by Scheme 1 and the attendant definitions, wherein X represents O; R represents independently for each occurrence methyl; and said chiral non-racemic catalyst is quinidine, (DHQ)$_2$PHAL, (DHQD)$_2$PHAL, (DHQ)$_2$PYR, (DHQD)$_2$PYR, (DHQ)$_2$AQN, (DHQD)$_2$AQN, DHQ-CLB, DHQD-CLB, DHQ-MEQ, DHQD-MEQ, DHQ-AQN, DHQD-AQN, DHQ-PHN, or DHQD-PHN.

In certain embodiments, the method of the present invention is represented by Scheme 1 and the attendant definitions, wherein the enantiomeric excess or diastereomeric excess of the product is greater than about 50%.

In certain embodiments, the method of the present invention is represented by Scheme 1 and the attendant definitions, wherein the enantiomeric excess or diastereomeric excess of the product is greater than about 70%.

In certain embodiments, the method of the present invention is represented by Scheme 1 and the attendant definitions, wherein the enantiomeric excess or diastereomeric excess of the product is greater than about 90%.

Nucleophiles

Nucleophiles, i.e., silyl cyanides, useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of appropriate reactants and conditions—in comparison with the rate of the desired reaction(s).

Silyl cyanides which satisfy the above criteria can be chosen for each substrate and will vary according to the substrate structure and the desired product. Routine experimentation may be necessary to determine the preferred silyl cyanide for a given transformation. In certain embodiments, the nucleophile may be part of the substrate, thus resulting in an intramolecular reaction.

Substrates

As discussed above, a wide variety substrates selected from the group consisting of ketones, aldehydes, thioketones, thioaldehydes, imines and hydrazones are effective in the methods of the present invention. In preferred embodiments, the substrate is a ketone or aldehyde. For example, the choice of ketone or aldehyde substrate will depend on factors such as the silyl cyanide to be employed and the desired product. In all embodiments, an appropriate substrate will be apparent to the skilled artisan. It will be understood that the substrate preferably will not contain any functionalities that interfere with the asymmetric cyanosilylation of the present invention. In general, an appropriate substrate will contain at least one reactive carbon-heteroatom double bond, e.g., carbonyl moiety, to which a silyl cyanide may add with the assistance of the catalyst.

Most of the substrates contemplated for use in the methods of the present invention contain a single ketone carbonyl moiety. Examples of suitable ketone substrates in the subject methods are depicted in the Figures.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions that will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −60° C. to −20° C.

In general, the asymmetric synthesis reactions of the present invention are carried out in a liquid reaction medium. The reactions may be run without addition of solvent, e.g., where the nucleophile is a liquid. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent that is not inert to the substrate under the conditions employed, e.g., use of ethanol as a solvent when ethanol is the desired nucleophile. In embodiments where water and hydroxide are not preferred nucleophiles, the reactions can be conducted under anhydrous conditions. In certain embodiments, ethereal solvents are preferred. In embodiments where water and hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, kinetic resolutions with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis methods of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

EXEMPLIFICATION

The invention now being generally described, it will be more readily understood by reference to the following examples that are included merely for purposes of illustration of certain aspects and embodiments of the present invention, and are not intended to limit the invention.

Example 1

General Procedure for the Catalytic Asymmetric Cyanosilylation of Ketones and Aldehydes

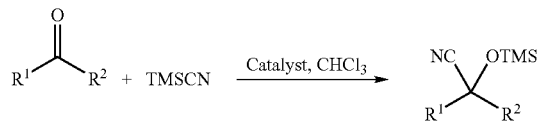

To a solution of ketone or aldehyde (0.20 mmol) and modified cinchona alkaloid ("catalyst", 2 mol %) in chloroform (0.20 mL), at −50° C. or −60° C., was added dropwise TMSCN (2.5–3.0 equiv). The reaction was monitored using GLC. After the reaction was complete, methanol (40 µL) was added, and the resulting mixture was stirred for 5 minutes. The mixture was diluted with hexanes (5.0 mL), and washed successively with aq. 0.2 N HCl (2×1.5 mL) and water (2×1.0 mL). The organic layer was collected, dried over $Na_2SO_4$, and concentrated. The residue was purified by column chromatography (acetone:hexanes, 1:100) to give the product. See FIGS. 3–11.

Example 2

General Procedures for the Preparation of α,α-Dialkoxy-Substituted Ketones

A. Prepared from Diethoxyacetonitrile

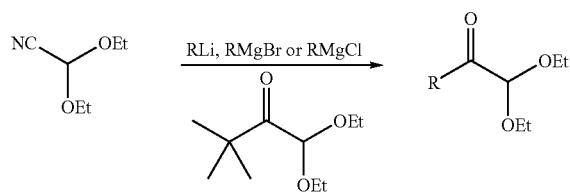

The reaction mixture of diethoxyacetonitrile and t-BuLi (1.7 M in hexane, 1.0 eq.) was stirred for 0.5 h and the product was obtained as a colorless oil in 56% yield. $^1$H NMR (400 MHz, CDCl$_3$) δ 1.21 (s, 9H), 1.24 (d, J=7.0 Hz, 6H), 3.53–3.62 (m, 2H), 3.64–3.72 (m, 2H), 5.04 (s, 1H); $^{13}$C NMR (100 MHz, CDCl$_3$) δ 15.29, 26.49, 43.13, 62.60, 98.92, 208.64.

B. Prepared from Arylglyoxal Monohydrates

To a suspension of phenylglyoxal monohydrate (761 mg, 5.00 mmol) in toluene or benzene (20 mL) was added alcohol (50.0 mmol) and PTS (86 mg, 0.50 mmol). After being refluxed, the mixture was cooled to room temperature and then concentrated. The residue was purified by silica gel column chromatography (acetone:hexanes/1:100) to give the desired product.

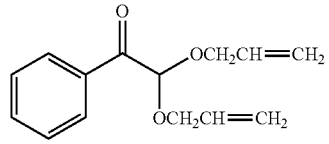

The mixture of phenylglyoxal monohydrate and allyl alcohol was refluxed in benzene for 2 h. The product was obtained as a colorless oil in 55% yield. $^1$H NMR (400 MHz, CDCl$_3$) δ 4.18 (dd, J=12.8, 6.0 Hz, 2H), 4.24 (dd, J=12.8, 5.2 Hz, 2H), 5.21 (d, J=10.4 Hz, 2H), 5.31 (d, J=17.6 Hz, 2H), 5.38 (s, 1H), 5.87–5.98 (m, 2H), 7.46 (t, J=7.6 Hz, 2H), 7.57 (t, J=7.4 Hz, 1H), 8.15 (d, J=7.6 Hz, 2H); $^{13}$C NMR (100 MHz, CDCl$_3$) δ 68.53, 101.19, 116.81, 118.15, 128.58, 128.71, 129.94, 133.75, 193.68; IR (neat) ν 3071, 1688, 1600, 1584, 1453 cm$^{-1}$; HRMS (EI) Calcd for $C_{14}H_{17}O_3$ (MH$^+$) 233.1178, found 233.1140.

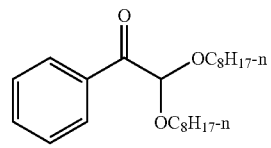

The mixture of phenylglyoxal monohydrate and n-octyl alcohol was refluxed in toluene for 2 h. The product was obtained as a colorless oil in 100% yield. $^1$H NMR (400 MHz, CDCl$_3$) δ 0.87 (t, J=7.2 Hz, 6H), 1.18–1.29 (m, 20H), 1.55–1.65 (m, 4H), 3.53–3.60 (m, 2H), 3.65–3.72 (m, 2H), 5.23 (s, 1H), 7.42–7.47 (m, 2H), 7.51–7.57 (m, 1H), 8.16 (d, J=7.2 Hz, 2H); $^{13}$C NMR (100 MHz, CDCl$_3$) δ 14.29, 22.85, 26.23, 29.42, 29.47, 29.84, 31.99, 68.05, 103.25, 128.49, 128.69, 130.13, 133.60, 194.39; IR (neat) ν 2923, 1691, 1599, 1467 cm$^{-1}$; HRMS (EI) Calcd for $C_{24}H_{41}O_3$ (MH$^+$) 377.3056, found 377.3031.

C. Prepared by Exchanging Dialkoxy Groups

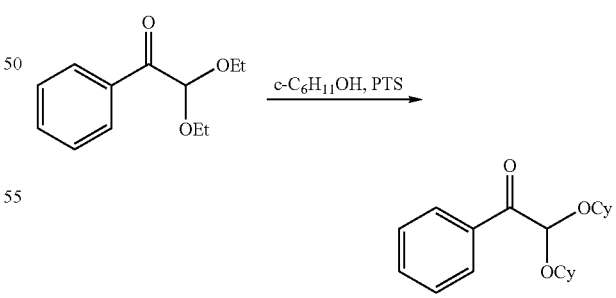

To a solution of 2,2-diethoxyacetophenone (1.04 g, 5.00 mmol) and cyclohexanol (10.0 g, 100 mmol) in toluene (30 mL) was added PTS (86 mg, 0.50 mmol). The mixture was refluxed for 2 h. The solvent was distilled and the remaining cyclohexanol was removed under reduced pressure. The residue was purified by silica gel column chromatography (acetone:hexanes/1:100) to give the product as a colorless oil (1.52 g, 96%). $^1$H NMR (400 MHz, CDCl$_3$) δ 1.13–1.38 (m, 8H), 1.39–1.54 (m, 4H), 1.59–1.83 (m, 6H), 1.87–1.97 (m, 2H), 3.59–3.67 9m, 2H), 5.26 (s, 1H), 7.39–7.46 (m, 2H), 7.54 (t, J=7.4 Hz, 1H), 8.23 (d, J=7.6 Hz, 2H); $^{13}$C NMR (100MHz, CDCl$_3$) δ 24.05, 24.26, 25.72, 32.52, 33.20, 76.40, 102.06, 128.26, 130.50, 133.31, 133.74, 195.36; IR (neat) ν 2933, 1689, 1598, 1580, 1449 cm$^{-1}$; HRMS (EI) Calcd for C$_{20}$H$_{29}$O$_3$ (MH$^+$) 317.2117, found 317.2098.

Example 3

Effect of Solvent on Asymmetric Cyanosilylation of a Ketone

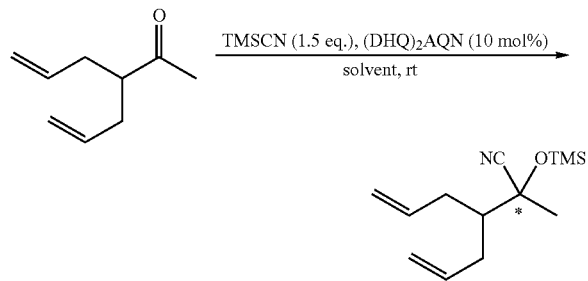

Figure 12:
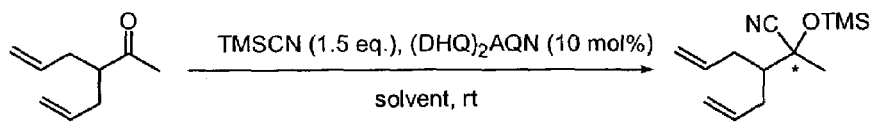
FIG. 12 tabulates the results of the catalytic asymmetric cyanosilylation of a ketone using (DHQ)$_2$AQN as the catalyst according to the methods of the present invention as a function of the solvent used.

To a solution of the ketone (13.8 mg, 0.10 mmol) and (DHQ)$_2$AQN (8.6 mg, 10 mol %) in solvent (0.10 mL) at room temperature was added trimethylsilyl cyanide (14.9 mg, 0.15 mmol). The mixture was allowed to stand for 4–24 h without stirring. The reaction was monitored with normal and chiral GC to determine the P/(P+S) value (where P is the peak integration for the product and S is for the starting material) and the enantiomeric excess of the product. The results are tabulated in FIG. 12.

Example 4

Effect of Solvent on Asymmetric Cyanosilylation of a Ketone

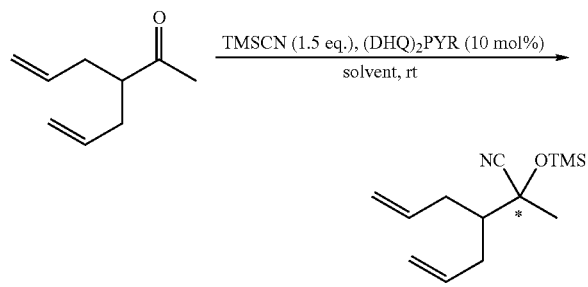

Figure 13:
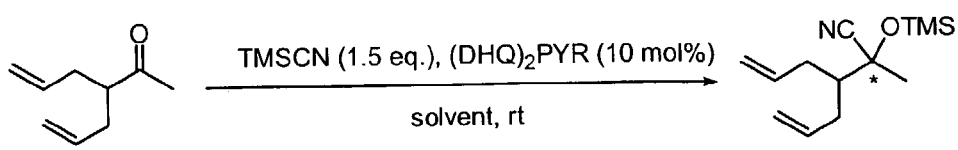
FIG. 13 tabulates the results of the catalytic asymmetric cyanosilylation of a ketone using (DHQ)$_2$PYR as the catalyst according to the methods of the present invention as a function of the solvent used.

To a solution of the ketone (13.8 mg, 0.10 mmol) and (DHQ)$_2$PYR (10 mol %) in solvent (0.10 mL) at room temperature was added trimethylsilyl cyanide (14.9 mg, 0.15 mmol). The mixture was allowed to stand for 4–24 h without stirring. The reaction was monitored with normal and chiral GC to determine the P/(P+S) value (where P is the peak integration for the product and S is for the starting material) and the enantiomeric excess of the product. The results are tabulated in FIG. 13.

Example 5

Effect of Catalyst on Asymmetric Cyanosilylation of a Ketone

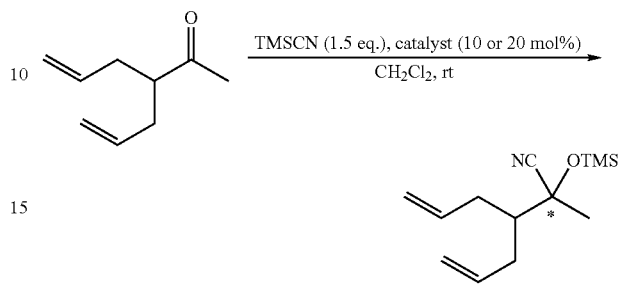

Figure 14:
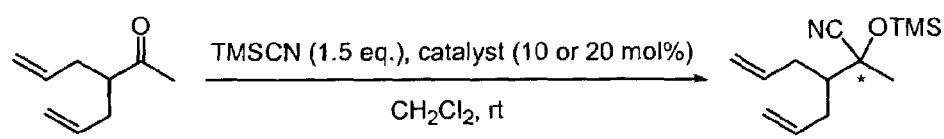
FIG. 14 tabulates the results of the catalytic asymmetric cyanosilylation of a ketone in methylene chloride according to the methods of the present invention as a function of the catalyst used.

To a solution of the ketone (17.4 mg, 0.10 mmol) and modified cinchona alkaloid (20 mol % for a monomer and 10 mol % for a dimer) in dichloromethane (0.10 mL) at room temperature was added trimethylsilyl cyanide (14.9 mg, 0.15 mmol). The mixture was allowed to stand for 4–24 h without stirring. The reaction was monitored as described in Example 3. The results are tabulated in FIG. 14.

Incorporation by Reference

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are encompassed by the following claims.

We claim:

1. A method of cyanosilylation of a substrate, comprising the step of combining a silyl cyanide, a substrate selected from the group consisting of ketones, aldehydes, thioketones, thioaldehydes, imines and hydrazones, and a chiral non-racemic catalyst, wherein said chiral non-racemic catalyst is a tertiary amine, phosphine or arsine, and wherein said chiral non-racemic catalyst catalyzes the addition of said silyl cyanide to said substrate to give a chiral non-racemic silyl cyanohydrin.

2. The method of claim 1, wherein said substrate is a ketone or aldehyde.

3. The method of claim 1, wherein said silyl cyanide is a trialkylsilyl cyanide.

4. The method of claim 1, wherein said silyl cyanide is trimethylsilyl cyanide.

5. The method of claim 1, wherein said chiral non-racemic catalyst is a tertiary amine.

6. The method of claim 1, wherein said chiral non-racemic catalyst is a cinchona alkaloid.

7. The method of claim 1, wherein said chiral non-racemic catalyst is quinidine, (DHQ)$_2$PHAL, (DHQD)$_2$PHAL, (DHQ)$_2$PYR, (DHQD)$_2$PYR, (DHQ)$_2$AQN, (DHQD)$_2$AQN, DHQ-CLB, DHQD-CLB, DHQ-MEQ, DHQD-MEQ, DHQ-AQN, DHQD-AQN, DHQ-PHN, or DHQD-PHN.

8. The method of claim 1, wherein said substrate is a ketone or aldehyde; and said silyl cyanide is a trialkylsilyl cyanide.

9. The method of claim 1, wherein said substrate is a ketone or aldehyde; said silyl cyanide is a trialkylsilyl cyanide; and said chiral non-racemic catalyst is a tertiary amine, phosphine or arsine.

10. The method of claim 1, wherein said substrate is a ketone or aldehyde; said silyl cyanide is a trialkylsilyl cyanide; and said chiral non-racemic catalyst is a tertiary amine.

11. The method of claim 1, wherein said substrate is a ketone or aldehyde; said silyl cyanide is a trialkylsilyl cyanide; and said chiral non-racemic catalyst is a cinchona alkaloid.

12. The method of claim 1, wherein said substrate is a ketone or aldehyde; said silyl cyanide is a trialkylsilyl cyanide; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

13. The method of claim 1, wherein said substrate is a ketone or aldehyde; said silyl cyanide is trimethylsilyl cyanide; and said chiral non-racemic catalyst is a tertiary amine, phosphine or arsine.

14. The method of claim 1, wherein said substrate is a ketone or aldehyde; said silyl cyanide is trimethylsilyl cyanide; and said chiral non-racemic catalyst is a tertiary amine.

15. The method of claim 1, wherein said substrate is a ketone or aldehyde; said silyl cyanide is trimethylsilyl cyanide; and said chiral non-racemic catalyst is a cinchona alkaloid.

16. The method of claim 1, wherein said substrate is a ketone or aldehyde; said silyl cyanide is trimethylsilyl cyanide; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

17. The method of claim 1, wherein the enantiomeric excess or diastereomeric excess of the chiral non-racemic silyl cyanohydrin is greater than about 50%.

18. The method of claim 1, wherein the enantiomeric excess or diastereomeric excess of the chiral non-racemic silyl cyanohydrin is greater than about 70%.

19. The method of claim 1, wherein the enantiomeric excess or diastereomeric excess of the chiral non-racemic silyl cyanohydrin is greater than about 90%.

20. A method of asymmetric cyanosilylation represented by Scheme 1:

Scheme 1

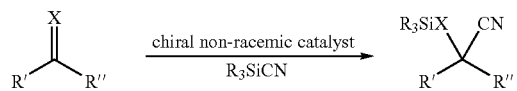

wherein
X represents O, S, NR', or NN(R')(R");
R represents independently for each occurrence alkyl, cycloalkyl, aryl, heteroaryl, aralkyl, or heteroaralkyl;
R' represents independently for each occurrence alkyl, cycloalkyl, alkenyl, alkynyl, aryl, heteroaryl, aralkyl, or heteroaralkyl;

R" represents independently for each occurrence H, alkyl, cycloalkyl, alkenyl, alkynyl, aryl, heteroaryl, aralkyl, or heteroaralkyl;
R' and R" are not identical;
the product is chiral and non-racemic; and
chiral non-racemic catalyst is a chiral non-racemic tertiary amine, phosphine, or arsine.

21. The method of claim 20, wherein X represents O.

22. The method of claim 20, wherein R represents independently for each occurrence alkyl.

23. The method of claim 20, wherein R represents independently for each occurrence methyl.

24. The method of claim 20, wherein said chiral non-racemic catalyst is a chiral non-racemic tertiary amine.

25. The method of claim 20, wherein said chiral non-racemic catalyst is a cinchona alkaloid.

26. The method of claim 20, wherein said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

27. The method claim 20, wherein X represents O; and R represents independently for each occurrence alkyl.

28. The method of claim 20, wherein X represents O; R represents independently for each occurrence alkyl; and said chiral non-racemic catalyst is a chiral non-racemic tertiary amine.

29. The method of claim 20, wherein X represents O; R represents independently for each occurrence alkyl; and said chiral non-racemic catalyst is a cinchona alkaloid.

30. The method of claim 20, wherein X represents O; R represents independently for each occurrence alkyl; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

31. The method of claim 20, wherein X represents O; and R represents independently for each occurrence methyl.

32. The method of claim 20, wherein X represents O; R represents independently for each occurrence methyl; and said chiral non-racemic catalyst is a chiral non-racemic tertiary amine.

33. The method of claim 20, wherein X represents O; R represents independently for each occurrence methyl; and said chiral non-racemic catalyst is a cinchona alkaloid.

34. The method of claim 20, wherein X represents O; R represents independently for each occurrence methyl; and said chiral non-racemic catalyst is quinidine, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

35. The method of claim 20, wherein the enantiomeric excess or diastereomeric excess of the product is greater than about 50%.

36. The method of claim 20, wherein the enantiomeric excess or diastereomeric excess of the product is greater than about 70%.

37. The method of claim 20, wherein the enantiomeric excess or diastereomeric excess of the product is greater than about 90%.

* * * * *